United States Patent [19]

Matsuda et al.

[11] Patent Number: 5,260,211
[45] Date of Patent: Nov. 9, 1993

[54] PROCESS FOR CULTIVATING ADHESIVE CELLS IN A PACKED BED OF SOLID CELL MATRIX

[75] Inventors: Yoshiaki Matsuda, Souwa; Shinjiro Mitsuda, Hasuda; Eitaro Kumazawa, Oyama; Atushi Baba, Ishibashi; Masakatsu Uesaka, Kawaguchi, all of Japan

[73] Assignee: Snow Brand Milk Products Co., Ltd., Hokkaido, Japan

[21] Appl. No.: 617,644

[22] Filed: Nov. 26, 1990

[30] Foreign Application Priority Data

Dec. 7, 1989 [JP] Japan ............................. 1-318440
Dec. 26, 1989 [JP] Japan ............................. 1-337298

[51] Int. Cl.$^5$ .................... C12N 5/02; C12N 5/00; C12N 11/14; C12M 1/12
[52] U.S. Cl. ....................... 435/240.24; 435/240.23; 435/176; 435/311
[58] Field of Search ........... 435/240.2, 240.23, 240.24, 435/176, 284, 240.242, 311

[56] References Cited

U.S. PATENT DOCUMENTS

| | | | |
|---|---|---|---|
| 4,144,126 | 3/1979 | Burbidge | 435/240.24 |
| 4,542,101 | 9/1985 | Nees | 435/240.24 |
| 4,649,117 | 3/1987 | Familletti | 435/240.24 |
| 4,833,083 | 5/1989 | Saxena | 435/240.24 |
| 4,889,812 | 12/1989 | Guinn et al. | 435/311 |
| 4,894,342 | 1/1990 | Guinn et al. | 435/240.242 |

FOREIGN PATENT DOCUMENTS

| | | | |
|---|---|---|---|
| 2934328 | 8/1979 | Fed. Rep. of Germany | 435/240.24 |
| 1-091775 | 4/1989 | Japan | 435/240.24 |

Primary Examiner—Douglas W. Robinson
Assistant Examiner—Susan M. Weber
Attorney, Agent, or Firm—Griffin, Butler, Whisenhunt & Kurtossy

[57] ABSTRACT

A process and system for cultivating adhesive cells in a packed bed of solid cell matrix is disclosed. Adhesive cells are adhered to a solid cell matrix, preferably ceramic particles, and packed in a cell culture tank to form the packed bed. The culture medium is circulated through the packed bed in a direction. The circulating of the culture medium is then stopped and the direction of the medium being circulated is reversed. This periodic switching of the direction of the culture medium reduces channelling of the culture medium. The bottom or head of the culture tank can also contain a separator to trap any bubble existing in the culture medium or to trap any quantity of cell matrix possibly running out from the culture tank.

6 Claims, 8 Drawing Sheets

PROCESS FOR CULTIVATING ADHESIVE CELLS IN A PACKED BED OF SOLID CELL MATRIX

BACKGROUND OF THE INVENTION

This invention relates to a cell cultivating system to produce a target substance such as physiologically active substance and is useful to cultivate adhesive animal cells, particularly, the gene-transduced rodential cells which are prolific and require high concentration oxygen supply.

The well known processes of adhesive cell cultivation are generally classified into the suspending process (in homogeneous system) and the immobilizing process (in unhomogeneous system). Typical one of the suspending processes is so-called microcarrier process and, as the typical immobilizing process, the process is known, in which the cells are fixed on membrane or carrier.

(A) The microcarrier process in which the microcarrier is suspended in culture liquid to cultivate cells is disclosed, for example, in Japanese Patent Application Disclosure Gazette No. 1989-174376 proposed by inventors forming a part of the inventors of the present application and U.S. Pat. No. 4,904,601.

In such microcarrier processes of well known art, a vigorously stirred flow must be produced to assure uniform oxygen supply to the cells because the oxygen thus supplied is usually of a large quantity. However, a shearing force developed from the vigorous stirring often seriously damages the cells, causing the cell exfoliation.

(B) The well known immobilizing processes for cell cultivation include the process employing a mass of glass-wool as the cell matrix as disclosed in Japanese Patent Application Disclosure Gazette No. 1986-25483, the process employing a porous structure in the form of the steric screen as the cell matrix as disclosed in Japanese Patent Application Disclosure Gazette No. 1989-86870 and the process employing ceramic material as the cell matrix as disclosed in Japanese Patent Application Disclosure Gazette No. 1988-158715.

Of the well known immobilizing processes for cell cultivation, those employing, as the cell matrix, the mass of glass-wool, the porous structure in the form of the cylindrical screen and the regular-shaped ceramic particles, respectively, are disadvantageous commonly in that the culture medium passages are apt to be fixed and so-called channeling occurs. The term "channeling" used herein indicates a phenomenon that the cells deviating from the culture medium passages are destructed or inactivated.

To avoid such phenomenon resulting in closure or fixation of the culture medium passages, various researches and developments have been made on material and configuration of the carrier.

In addition to said channeling phenomenon, the prior art has encountered a serious problem such that continuous supply of the culture medium in a single direction often causes a significant gradient in concentrations of nutrient, pH and DO between inlet and outlet of the packed bed filled with the cell matrix and, in consequence, unevenness in cell proliferation as well as production of physiologically active substance.

Specifically, culture medium supply in a single direction often results in shortage of oxygen and increases waste product of the cells in the proximity of the outlet, adversely affecting the proliferation of the cells and production of the target substance. While accelerated circulation of the culture medium might solve such problem and thereby uniformalize the oxygen supply, a circulating velocity for the culture medium is practically limited to a predetermined linear velocity, because circulation of the culture medium through the packed bed at an extremely high linear velocity will result in the cell exfoliation caused by a shearing force of the stirred flow.

Moreover, the culture medium intrinsically tends to bubble since the culture medium is adequately supplied with oxygen and contains in itself the ingredients promoting the bubbling such as protein. Staying of such bubbles in the packed bed filled with the cell matrix also causes the channeling.

Though it is a commonly adopted technique to adjust dissolved oxygen concentration in a culture medium tank separately of the cell cultivating tank, it is also known to perform the adjustment of the extracellular environment within the cell cultivating tank. Specifically, Japanese Patent Application Disclosure Gazette No. 1985-9482 discloses such suspending process in which the culture medium is supplied together with air directly into the cell cultivating tank and the culture medium is separated from its supernatant liquid by the precipitator of cone type. With this process of prior art, however, the culture medium is directly mixed with air within the cell cultivating tank without relying on any particular mixing technique and therefore no sufficient mixing effect can be expected. Furthermore, supply of the culture medium is carried out merely by using a stirring propeller rotating in a constant direction, so uniform air supply is difficult.

While Japanese Patent Application Disclosure Gazette No. 1989-215276 discloses an example of the immobilizing process in which there are provided holding means for the cell matrix and the circulation circuit for the culture medium adjustment, the direction in which the culture medium is supplied is constant and therefore the above-mentioned problem is never solved by this process of prior art.

SUMMARY OF THE INVENTION

It is an object of the invention to provide a cell cultivating system adapted to uniformalize concentrations of nutrient, pH and DO supplied into a culture tank filled with cell matrix so as to improve a proliferating efficiency for adhesive animal cells, particularly, gene-transduced rodential cells, to avoid a channeling and to deal with cell cultivation requiring to be supplied with oxygen of high concentration.

The object set forth above is achieved, in accordance with the invention, by a process for cell cultivation generally including steps of:

keeping adhesive cells clinging to a cell matrix;

filling said cell matrix into a culture tank;

storing culture medium used to cultivate said cells clinging to said cell matrix in a medium recirculating tank and sparging said culture medium with oxygen containing gas; and supplying the culture tank with said culture medium to obtain a target product, said process for cell cultivation being characterized by steps of:

supplying the culture tank with the culture medium by circulating the culture medium between said culture tank and said medium recirculating tank in a predetermined direction for a certain time;

supplying the culture tank with the culture medium by circulating the culture medium between said culture tank and said medium recirculating tank in a direction other than said predetermined direction for a certain time; and thereby periodically switching the direction in which the culture medium is supplied to the culture tank.

This process is implemented, in accordance with above-mentioned aspect of the invention, by a cell cultivating system comprising:

a culture tank provided with upper and lower ports and filled with a cell matrix having adhesive cells clinging thereto;

a medium recirculating tank connected in a fluid communicating relationship to said culture tank by supply and recovery lines and provided with means to sparge the culture medium with oxygen containing gas; and switching means for periodically switching a direction in which the culture medium is circulated during circulation of the culture medium between said culture tank and said medium recirculating tank.

According to still another aspect of the invention, said process can be also implemented by a cell cultivating system comprising:

a packed bed filled with a cell matrix having adhesive cells clinging thereto;

a culture tank containing said packed bed therein;

means to sparge a culture medium stored in said culture tank with oxygen containing gas;

a circulation circuit extending from a head of said culture tank through a circulation pump to a bottom of the packed bed; and means to switch a direction in which the culture medium is circulated along said circulation circuit.

According to further aspect of the invention, said process can also implemented by a cell cultivating system comprising:

a packed bed filled with a cell matrix having adhesive cells clinging thereto;

a culture tank provided therein with said packed bed immersed in a fluid communicating relationship to said culture tank for circulation of the culture medium;

means provided within said medium recirculating tank to sparge the culture medium with oxygen containing gas; and a rotary blade provided above or below said packed bed adapted to be rotated in a direction being periodically switched.

According to further another aspect of the invention, said process can be also implemented by a cell cultivating system comprising:

a packed bed filled with a cell matrix having adhesive cells clinging thereto;

a culture tank provided therein with said packed bed immersed below a liquid level of culture medium;

a cylindrical member having upper and lower openings, and mounted within said culture tank so as to surround said packed bed;

a rotary blade provided above or below said packed bed adapted to be rotated in a direction being periodically switched; and means provided within said culture tank to sparge the culture medium with oxygen containing gas.

The technical measure mentioned just above is particularly advantageous to obtain a compact cell cultivating system.

Generally in cultivation of adhesive animal cells, not only nutrient but also dissolved oxygen to be supplied to the culture medium must be carefully controlled as the most important factors for the process management. Particularly, the gene-transduced rodential cells are often cultivated at high density and oxygen consumption is correspondingly high. The dissolved oxygen is meaningfully related to a productivity of the target substance and this productivity is lowered as the dissolved oxygen is reduced.

The culture tank filled with the cell matrix has usually encountered a structural problem due to a relatively long distance along which the culture medium must travel from the inlet to the outlet thereof. Specifically, the adhesive cells are certainly supplied with sufficient oxygen to proliferate in the proximity of the culture medium inlet but the quantity of oxygen supplied to the cells significantly decreases in the proximity of the culture medium outlet and amount of the waste product from the cell correspondingly increases.

As has previously been mentioned, excessively accelerated circulation of the culture medium through the culture tank would cause undesirable cell exfoliation, and a series of experiments indicated that it is rather preferred to maintain the circulating velocity of the culture medium at a linear velocity less than 15 cm/min.

Under such restricted circulating velocity of the culture medium through the culture tank, circulation of the culture medium in a single direction would cause the channeling, the passage fixation and the stagnation of the culture medium. Stagnation of the culture medium necessarily results in increased concentrations of carbon dioxide and lactic acid and shortage of the dissolved oxygen, finally leading to death of the cells. Switching of the culture medium circulating direction according to the invention is sufficiently effective to overcome this problem.

Conventionally, the channeling has been one of the most serious problems encountered by the cell cultivating system particularly when ceramic carrier or fibrous carrier are used as the cell matrix, because it is intrinsically difficult for such carrier to be subjected to stirring. The invention solves this problem by said switching of the circulating direction.

Particularly when irregular-shaped ceramic particles are used as the cell matrix, the individual ceramic particles have no surface contacts with one another, assuring a large cultivating area, and the channeling can be effectively avoided merely by switching the circulating direction so as to provide new passages available for the culture medium. Switching of the circulating direction also eliminates one-sided oxygen supply to the cells and thus uniformalizes the cell condition throughout the culture tank.

Provision of a bubble separator is very effective to avoid the channeling as well as the cell exfoliation on the individual ceramic particles.

BRIEF DESCRIPTION OF THE DRAWINGS

The above and other objects of the invention will be seen by reference to the description taken in connection with the accompanying drawings, in which.

DETAILED DESCRIPTION OF THE INVENTION

The invention will be more apparently understood from the following description of preferred embodiments made in reference with the accompanying drawings.

Figure 1:
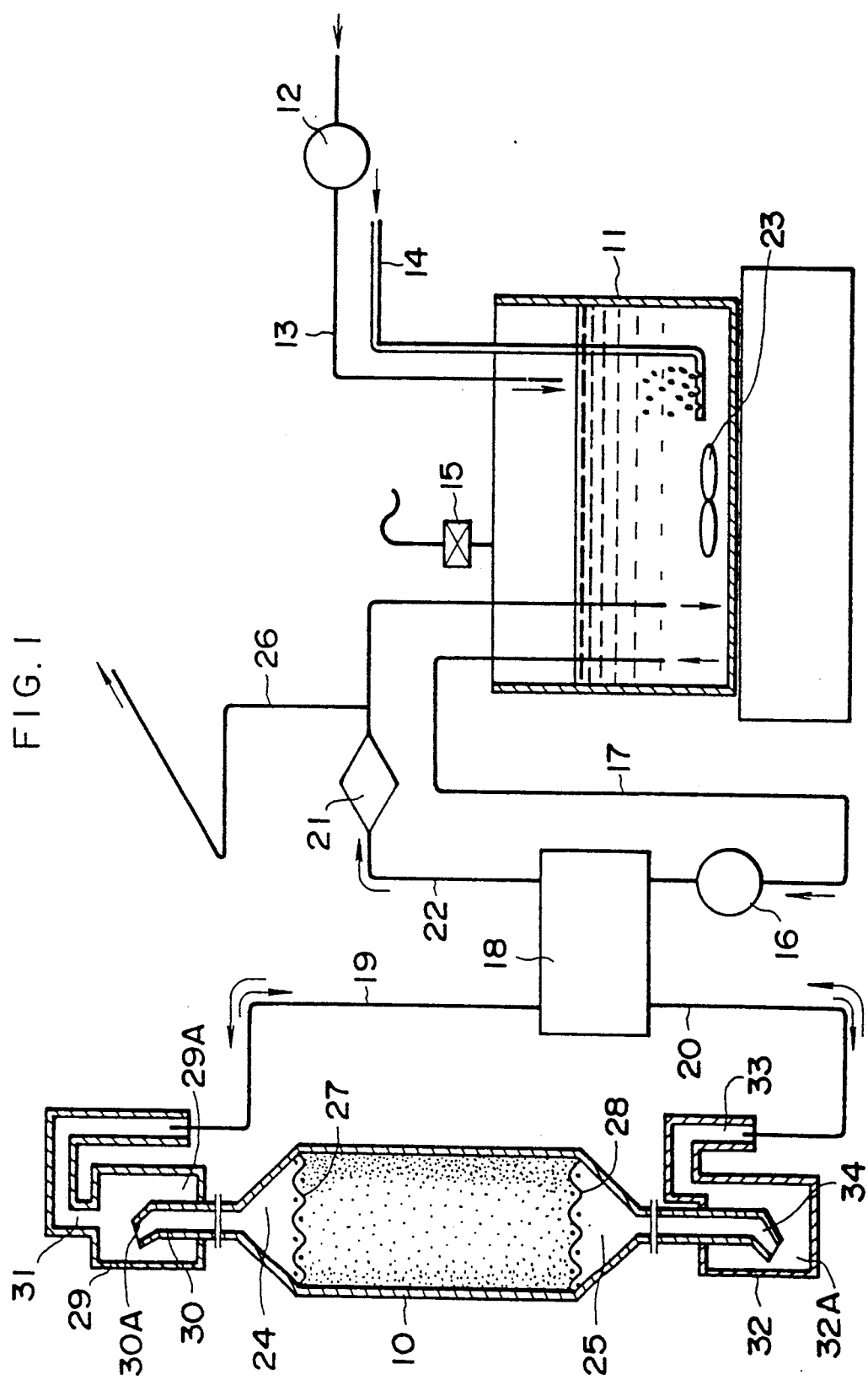
FIG. 1 is a schematic diagram illustrating a first embodiment of the system constructed in accordance with the invention.

Referring to FIG. 1, the first embodiment of the system constructed according to the invention is illustrated. A medium recirculating tank 11 is adapted to be supplied with fresh culture medium through a supply line 13 under action of a pump 12 and sparged with gaseous oxygen through an oxygen supply line 14.

Within the medium recirculating tank 11, a concentration of dissolved oxygen in the culture medium is adjusted under action of a stirring blade 23 driven by an electromotor (not shown). It should be understood that a magnetic stirrer may be also used for the stirring.

The medium recirculating tank 11 is provided with a vent filter 15 which is, more specifically, mounted in a gas exhaust pipe provided on an upper portion of the medium recirculating tank 11 in order to discharge any excessive quantity of the gas supplied to the culture medium. Such filter is useful for decontamination of the culture medium.

The culture medium once stored within the medium recirculating tank 11 is supplied by a pump 16 through a line 17, a circulation switching device 18 comprising, for example, a solenoid value, then a line 19 and an upper port 24 into the culture tank 10. Upon activation of the circulation switching device 18, the culture medium is supplied through a line 20 and a lower port 25 of the culture tank 10 into said culture tank 10.

The culture medium thus supplied into the culture tank 10 returns through the circulation switching device 18 and then through a recovery line 22 having a DO sensor or dissolved oxygen detecting electrode 21 into the medium recirculating tank 11. For exchange of the culture medium, the quantity of spent culture medium can be withdrawn through a product separator line 26 followed by supplementing the corresponding quantity of fresh culture medium through the line 13 into the culture medium adjustment tank 11 under the action of the pump 12.

The culture tank 10 is filled between upper and lower carrier holding screens 27, 28 with irregular shaped ceramic particles.

There is provided above the upper port 24 an upper bubble separator 29 connected by an upper pipe 31 to the line 19. An inner pipe 30 connected to the upper port 24 is inserted into the upper bubble separator 29 and has a bent tip 30A. Axes of the upper bubble separator 29 and the inner pipe 30 are out of alignment with each other so that any bubble existing in the culture medium supplied through the upper pipe 31 is prevented thereby from directly entering the inner pipe 30.

With the upper bubble separator 29 being constructed as has been mentioned above, the bubble separation can be effectively achieved.

The lower port 25 is provided with a lower separator 32 adapted not only to separate any bubble existing in the culture medium but also to trap any carrier running out through the carrier holding screen 28. An inner pipe 34 connected to the lower port 25 has also a bent tip so that no bubble can directly enter the inner pipe 34. There is provided above the lower separator 32 an upper pipe 33 connected to the line 20.

This upper pipe 33 is necessary to facilitate a ventilation. The separator 32 includes a separating chamber 32A simultaneously defining a ceramic particle trap and an air trap. This separating chamber 32A differs from a separating chamber 29A in the upper bubble separator 29 which functions only as an air trap. More specifically, the quantity of air trapped within the separating chamber 32A or 29A without directly entering the culture tank when the fresh culture medium is supplied through the upper port 24 or the lower port 25 into the culture tank may be recovered through the line 20 or 19 into the medium recirculating tank 11 by switching the direction in which the culture medium is circulated.

During such circulation of the culture medium, any amount of fine carrier otherwise might run out through the holding screen 28 for the cell matrix-bed and get mixed into the culture medium circulating line, resulting in damage of the line as well as contamination of the culture medium as the latter is supplied through the upper port 24 into the culture tank 10. To avoid this, there is provided the above-mentioned separating chamber 32A adapted to, in addition to the bubble separating function, trap the fine ceramic particle serving as said fine carrier and thereby to prevent such fine carrier from being circulated through the line 20 into the other lines.

Based on experimental use of the fine carrier having a bulk specific gravity of from 3.9 to 4.3, it was found that the fine carrier once trapped within the separating chamber 32A does not fly up when supply of the culture medium through the lower port 25 at a flow rate of 50 l/hr.

The fine carrier once trapped by the lower separator 32 thus stays therein until the cultivation is completed and, upon completion of the cultivation, such fine carrier may be removed and washed for resuse thereof.

It should be noted here that such running out of the fine carrier through the holding screen 28 does not occur continuously as the time elapses but occurs only at initiation of the cultivation for every batch and the amount thereof is relatively small.

Figure 2:
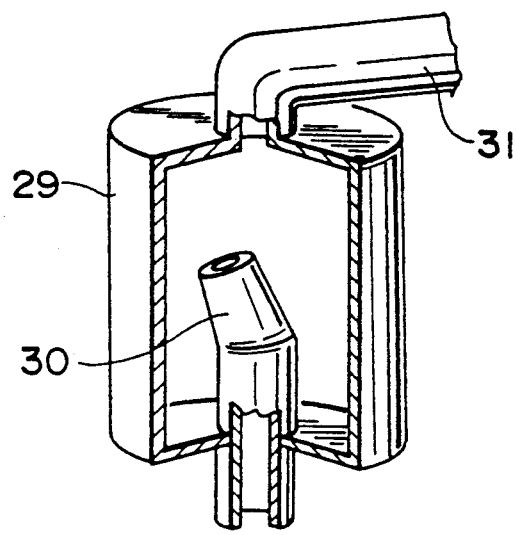
FIG. 2 is a perspective view illustrating, partially in section, a specific embodiment of the upper bubble separator in the system of FIG. 1.

FIG. 2 illustrates a specific embodiment of the upper bubble separator 29 with the inner pipe 30 inserted into the upper bubble separator 29 and having the bent tip 30A.

Figure 3:
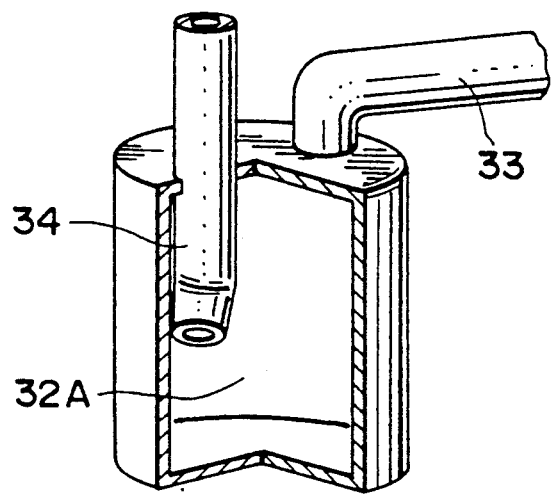
FIG. 3 is a view similar to FIG. 2 but illustrating a specific embodiment of the lower separator.

FIG. 3 illustrates a specific embodiment of the lower separator 32 in which the inner pipe 34 connected to the lower port 25 has its tip also bent so as to prevent any bubble from directly entering the inner pipe 34. Axes of the lower separator 32 and the associated inner pipe 34 are out of alignment with each other.

Figure 4:
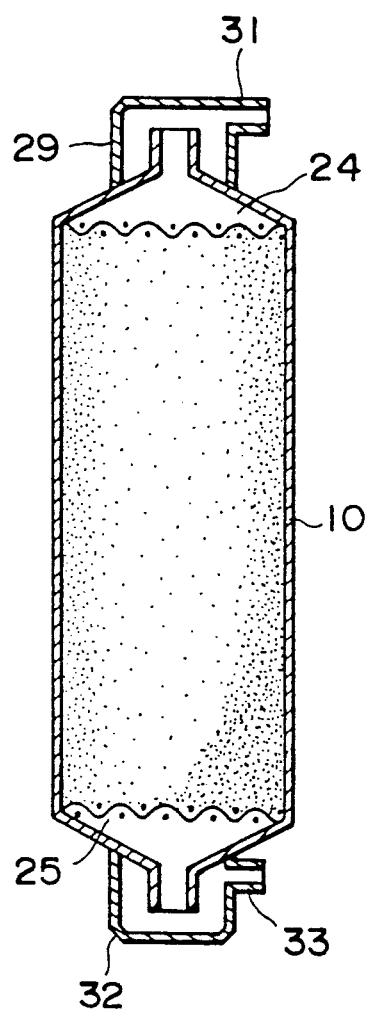
FIG. 4 is a sectional view illustrating, by way of example, the upper and lower separators of FIG. 1 constructed integrally with the culture tank.

FIG. 4 illustrates a specific embodiment of the upper bubble separator 29 and the lower separator 32 constructed integrally with the culture tank 10, in which said upper bubble separator 29 and said lower separator 32 are connected to funnel-shaped walls of said upper port 24 and said lower port 25, respectively, so that both the separating chambers of ports 24 and 25 readily trap the fine ceramic carrier and/or the air.

To verify an effect expected to be provided by the invention, a series of experiments were conducted concerning the switching of the culture medium circulating direction and the separating effect by the upper bubble separator 29 and the lower separator 32.

EXPERIMENT 1

Relative activity value was determined with the culture medium circulating direction being switched eight times per day and with the culture medium being supplied continuously through the lower port 25 toward the upper port 24 without switching this direction. From comparison of the activity values obtained under these two conditions, it was found that an activity value of 152% is achieved when the culture medium circulating direction is switched eight times per day relative to a reference value of 100% corresponding to the activity value (i.e., productivity) obtained with the culture medium being circulated continuously in the same direction, i.e., from the lower port 25 toward the upper port 24 without switching this direction.

EXPERIMENT 2

The culture tank provided with the upper bubble separator 29 and the lower separator 32, on one hand, and the culture tank having none of these separators were used and the culture medium circulating direction was switched eight times per day in these tanks. It was observed that, in the culture tank 10 having neither the upper bubble separator 29 nor the lower separator 32, bubble had increased day by day within the culture tank 10 until remarkable cracks had been formed among the cell matrix-bed, resulting in so-called channeling, cell ablation over the surface of the ceramic carrier and increased dead cells. Thus, effective cultivating process lasted only five to seven days.

With the culture tank 10 having both the upper bubble separator 29 and the lower separator 32, on the other hand, no bubble was observed and it was possible to maintain the cultivating process for three or more months. Concerning the relative activity value, the culture tank provided with both the upper bubble separator 29 and the lower separator 32 exhibited a value as high as 195% relative to a reference value of 100% corresponding to the value exhibited by the culture tank having neither the upper bubble separator 29 nor the lower separator 32.

In the system of the invention, as will be apparent from the foregoing description, provision of the lower separator is very useful when supply of the culture medium downwardly occurs upon alternate switching of the culture medium circulating direction, since the system otherwise would encounter various problems such that the fine ceramic carrier particles run out through the holding screen into the circulation lines, possibly resulting in damage of the pumps or the tubes defining the respective lines, sometimes causing crack, leakage and contamination of these components and joints thereof. Alternate switching of the culture medium circulating direction is useful also to avoid the previously mentioned channeling which otherwise would be unavoidable. Specifically, such alternate switching should be intermittently and repeatedly performed in view of the fact that a new channeling would occur if supply of the culture medium continues for a period longer than a predetermined period in a same direction.

Such alternate switching of the circulating direction is also effective to maintain within the culture tank substantially uniform concentration gradients of nutrient, pH, DO etc. and to eliminate occurrence of the channeling. In this manner, a substantially constant environment is established throughout the culture tank. It should be understood that a specific switching cycle largely depends on the particular design of the culture tank and must be empirically selected.

In an actual process of cultivating the genetransduced rodential cells to produce a target substance, during which a dissolved oxygen concentration of 100% is maintained at the inlet so as to ensure a dissolved oxygen concentration of 60 or higher % at the outlet of the culture tank, circulation of the culture medium in a fixed direction would cause a channeling and a visible discoloration in a given time. Though the average DO is maintained at a level of 60 or higher % at the outlet, it is supposed that, within the culture tank, there may be spots having the dissolved oxygen concentration varying from approximately 0% to approximately 100% along the passage of the culture medium so as to average 60 or higher % at the outlet.

In this way, the invention allows the undesirable channeling to be eliminated by alternately switching the culture medium direction. The invention also allows the dissolved oxygen concentration in the culture medium to be adjusted by monitoring the oxygen concentration at the outlet by the DO detector electrode 21, thereby avoiding consumption due to any excessive oxygen supply.

It should be understood that the medium recirculating tank 11 may be provided, if necessary, with auxiliary devices such as a level meter (not shown) and a level controller.

Figure 5:
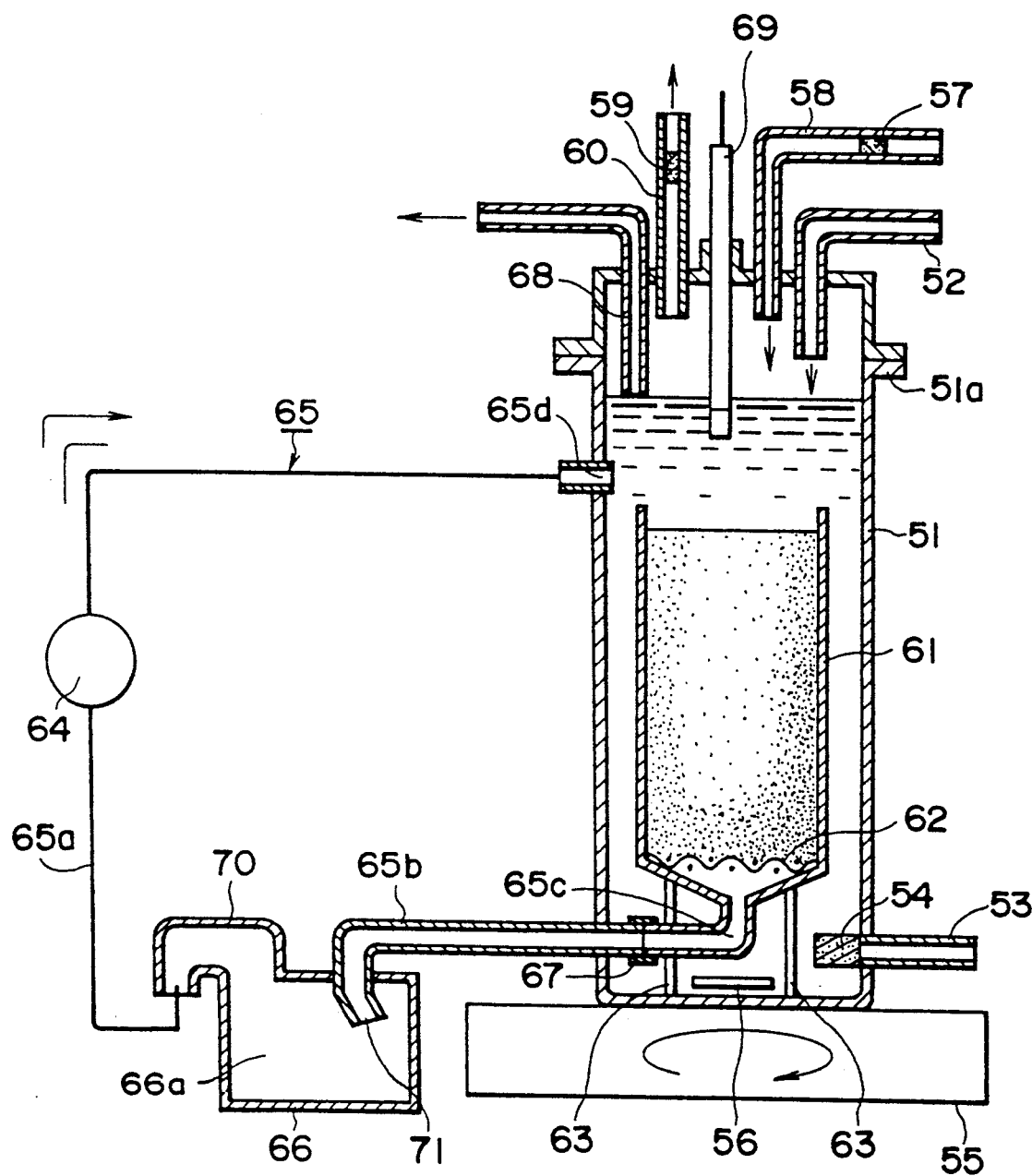
FIG. 5 is a diagram illustrating, partially in section, a second embodiment of the system constructed in accordance with the invention.

A second embodiment of the system constructed according to the invention will be described in reference with FIG. 5.

Fresh culture medium is supplied through a supply line 52 into a culture tank 51 from thereabove while gaseous oxygen is sparged through an oxygen supply line 53 connected to the bottom of the culture tank 51 into the bottom thereof through a filter 54.

A poker or stirring rod 56 of a magnet stirrer 55 provided on the bottom of the culture tank is activated to stir the interior of the culture tank 51 as the culture medium is supplied and the gaseous oxygen is sparged into culture tank 51 in the manner as mentioned just above so that the concentration of nutrient as well as dissolved oxygen in the culture medium may be effectively adjusted. It should be understood that the poker may be replaced by a motor-driven stirring blade.

Reference numeral 58 designates an air supply line provided therein with a filter 57, said air supply line being adapted to supply the air containing 5% carbon dioxide into head space defined within a head of the culture tank 51.

Purpose of the air thus supplied by the air supply line is to control pH of the culture medium within the culture tank 51. Any quantity of excessive air or gaseous oxygen remaining not dissolved in the culture medium is exhausted out of the culture tank 51 by an exhaust line 60 connected to the head of the culture tank 51 through a filter 59 contained by said exhaust line 60. The culture tank 51 contains therein a packed bed 61 immersed below the liquid surface and the packed bed 61 comprises irregular shaped ceramic particles serving as the cell matrix held by a holding screen 62. An additional holding screen may be provided above the packed bed 61 which is, in turn, provided with appropriate legs 63 so that the packed bed 61 may stand on its own legs 63.

Instead of providing the packed bed 61 with the legs 63, as in this embodiment, the packed bed 61 may be provided with a male or female structure adapted to be detachably mated with a corresponding female or male structure of the culture tank 51 or there may be provided between the packed bed wall and the culture tank wall a releasably locking means.

The legs may be replaced by a lower extension of the packed bed wall. However, such extension should be provided with appropriate openings so as to maintain a smooth circulation of the culture medium below the packed bed.

Furthermore, a male and female structure may be provided between the packed bed wall and the culture tank wall to suspend the packed bed 61.

Reference numeral 64 designates a circulation pump provided in a circulation line 65 to establish a fluid communication between a bottom of the packed bed 61 and a head of the culture tank 51. The culture medium within the culture tank 51 is supplied by said circulation pump 64 through an upper pipe 65d of the circulation line 65 extending below the liquid level of the culture tank 51 but above the packed bed 61 into said packed bed 61. Upon switching of the circulation pump 64, the culture medium is supplied through a lower pipe 65c of the packed bed 61 into said packed bed 61 and then recovered through said upper pipe 65d.

It is also provided that a quantity of the culture medium can be removed through a product recovery line 68 opening at the liquid level of the culture tank 51 and, upon such removal, the corresponding quantity of fresh culture medium is supplemented through the supply line 52 into the culture tank 51.

In this way, the liquid level of the culture tank 51 is controlled by the quantity of supplied culture medium so as to be flushed with the outlet port of the product recovery line 68.

At the head of the culture tank 51 there is provided a DO sensor or dissolved oxygen detector electrode 69 having its lower end immersed in the culture medium within the culture tank 51.

The circulation line 65 contains therein a separator 66 serving not only for bubble separation but also for carrier trapping between the bottom of the packed bed 61 and the circulation pump 64. A pipe 70 adapted to mount an upper pipe 65a connected to the circulation pump 64 on the separator 66 is appropriately curved and connected to the head of said separator 66 so that any bubble trapped therein may be readily relieved.

A lower pipe 65b connecting the separator 66 to the packed bed 61 has its opening end 71 so bent to prevent any bubble from directly entering the packed bed 61. Thus, the bubble, if any, is effectively trapped by a separation chamber 66a of the separator 66. When the culture medium is circulated through the upper pipe 65d, the packed bed 61 and then the lower pipe 65c, any fine carrier possibly running out through the holding screen 62 for the ceramic carrier is trapped by the separation chamber 66a.

Trapping the fine ceramic carrier by the separator 66 makes it possible to prevent such fine carrier possibly running out through the holding screen 62 from getting mixed into the culture medium circulation line and thereby to protect the culture medium against contamination due to a damage of the line.

The fine carrier once trapped by the separator 66 stays there until completion of cultivation and, after completion of cultivation, may be removed and washed for reuse thereof or discarded. The bubble trapped by the separation chamber 66a of the separator 66 is, upon switching of the culture medium circulating direction, brought back into the culture tank 51, ascends through the culture medium and is exhausted through the exhaust line 60.

Now a process of cell cultivation will be described. After the packed bed is inoculated with cells and the culture medium for proliferation is circulated until a predetermined number of cells are obtained, this culture medium is removed from the bottom of the culture tank 51 through an exhaust line (not shown). Then, the culture medium for production of physiologically active substance is supplied from a tank (not shown) into the culture tank 51 through the supply line 52 and the culture medium containing the physiologically active substance produced by the cells clinging to the carrier of the packed bed 61 is recovered through the line 68 followed by elution of said physiologically active substance using a column. When the cells clinging to the ceramic carrier no more produces the physiologically active substance, the culture medium is removed from the bottom of the culture tank 51 through an exhaust line (not shown) and the ceramic carrier is removed from the packed bed. Filling and removal of the ceramic carrier into and from the packed bed 61, respectively, are performed by opening a flanged head 51a of the culture tank 51.

Removal of the packed bed 61 from the culture tank 51 is performed by dismounting a joint pipe 67 connecting the lower pipe 65c to the other lower pipe 65b.

To open the head of the culture tank 51, the respective joint pipes associated with the culture medium supply line 52, the air supply line 58 and the product recovery line 68 are dismounted.

Figure 6:
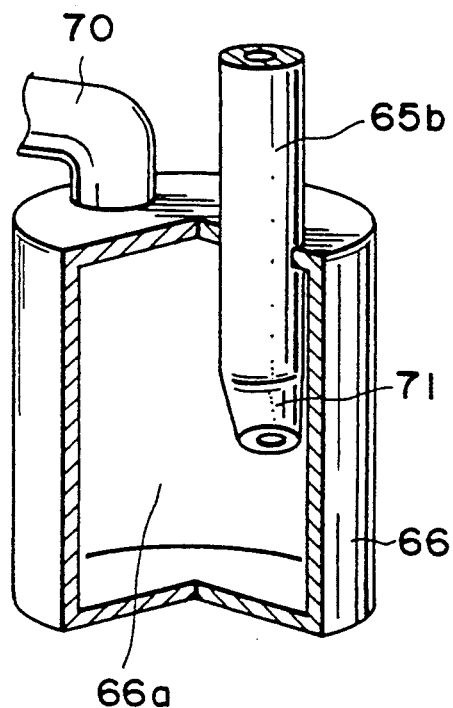
FIG. 6 is a view similar to FIG. 3 illustrating a specific embodiment of the separator in the system of FIG. 5.

FIG. 6 illustrates a specific embodiment of the separator 66 in which the lower pipe 65b has its end port 71 bent to prevent any bubble from directly entering the circulation line. Axes of the separator 66 and the lower pipe 65b are out of alignment with each other.

Figure 7:
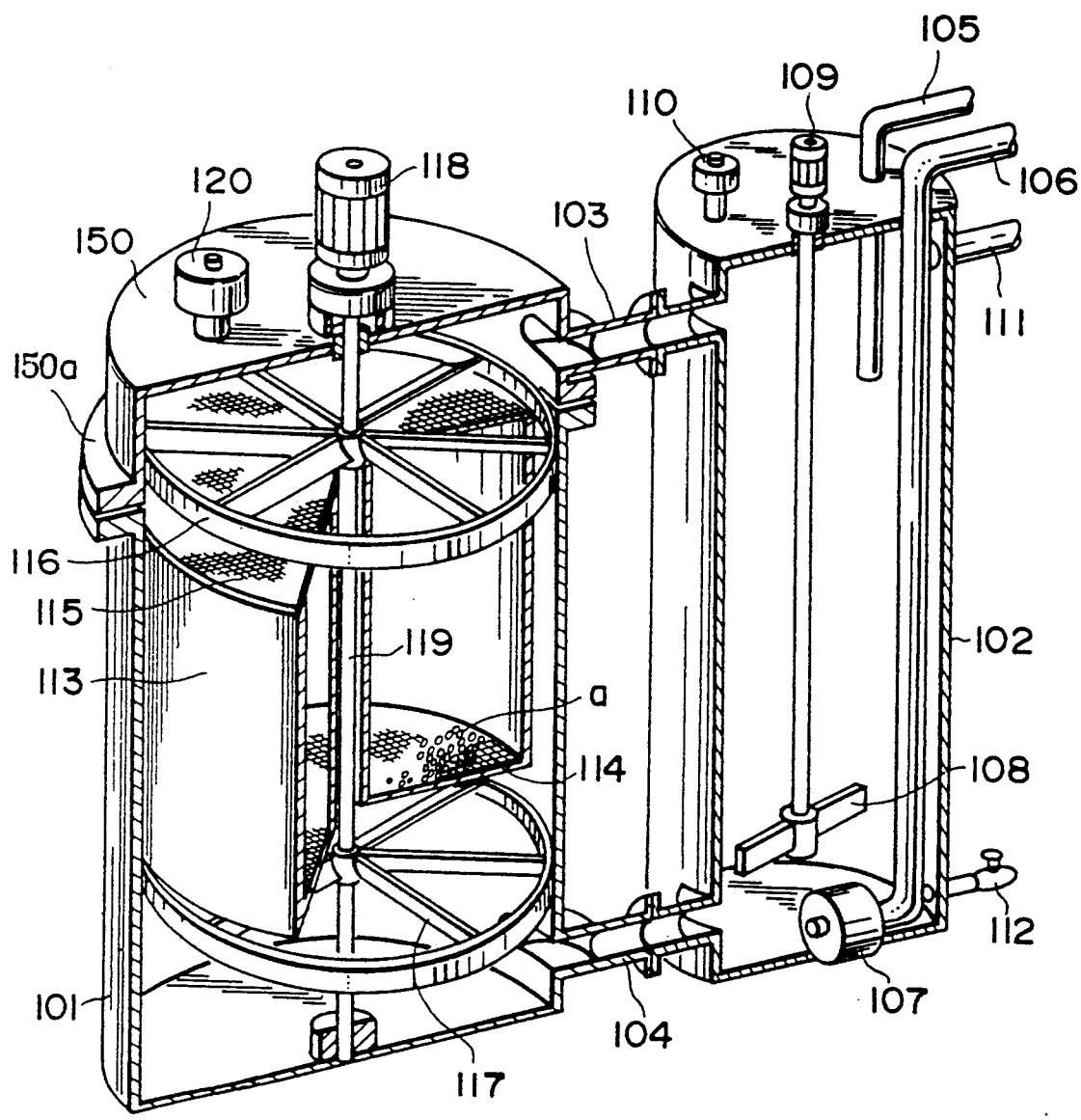
FIG. 7 is a perspective view illustrating, partially in section, a third embodiment of the system constructed in accordance with the invention.
Figure 8:
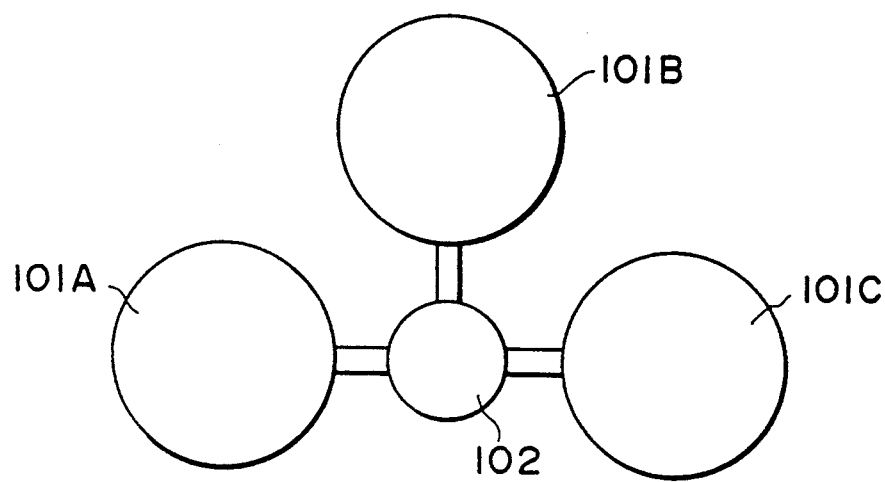
FIG. 8 is a diagram illustrating a specific embodiment of the medium recirculating tank in the system of FIG. 7 provided therearound with a plurality of culture tanks.
Figure 9:
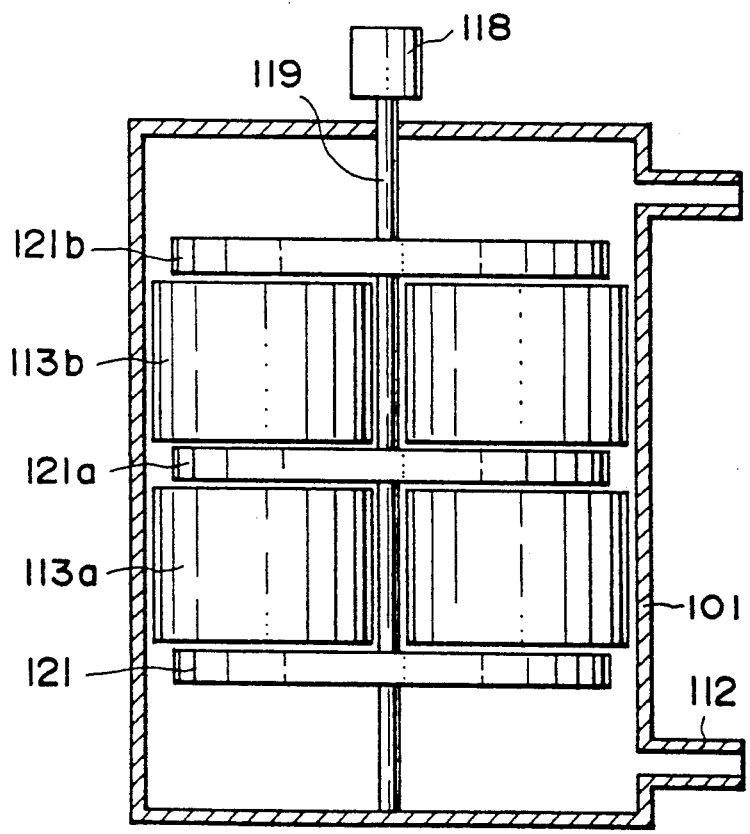
FIG. 9 is a sectional view illustrating a specific embodiment of the packed bed in the system of FIG. 7 arranged in a multistage fashion and provided between respective pairs of adjacent stages with rotary blades.
Figure 10:
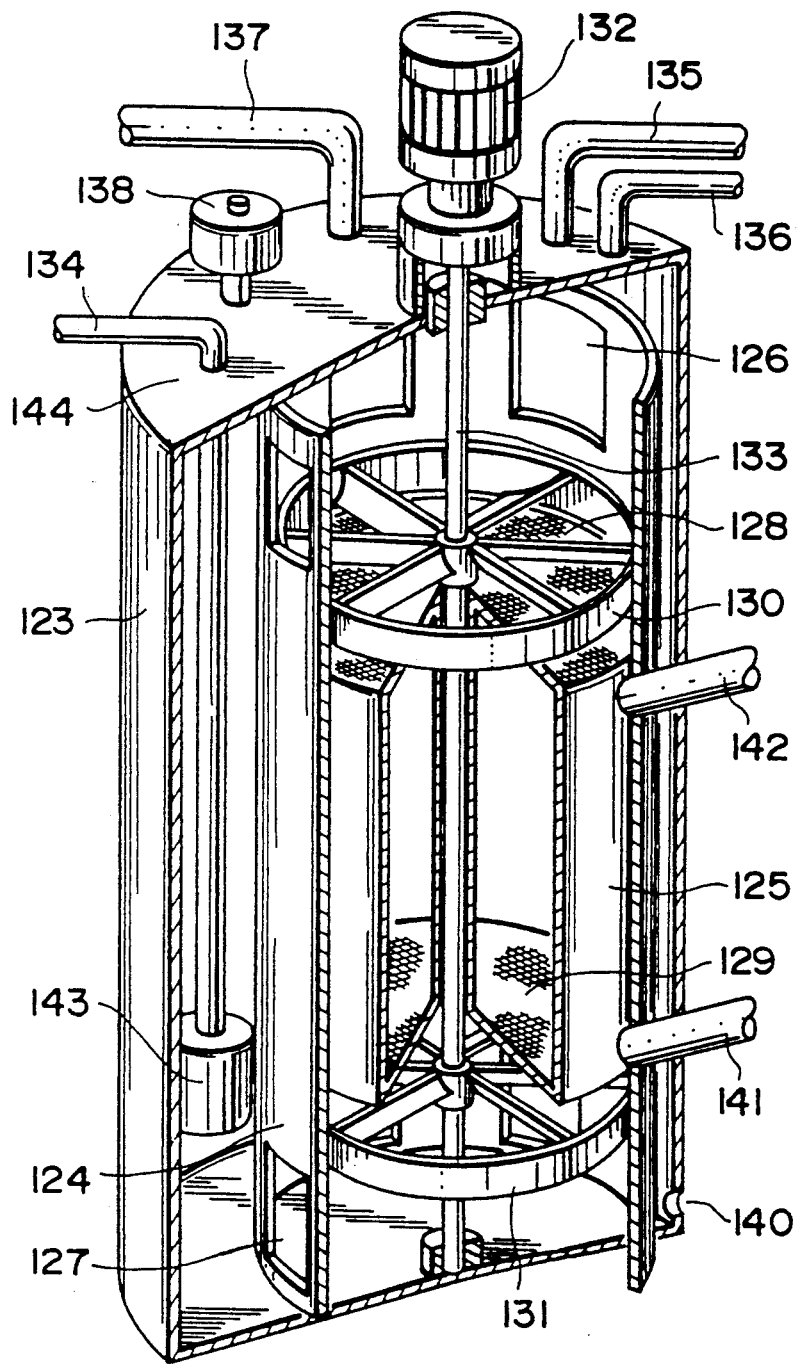
FIG. 10 is a view similar to FIG. 7 but illustrating a fourth embodiment of the system constructed in accordance with the invention.

A third embodiment of the system constructed according to the invention will be described in reference with FIG. 7.

tank 123 so that the air sparging required to supply the culture medium with oxygen can be performed in the larger gap defined between the cylindrical member 124 and the culture tank 123.

Reference numeral 134 designates an air supply line adapted for sparging through a filter 143.

Piping for supply and recovery of the culture medium are also arranged in said larger gap defined between the cylindrical member 124 and the culture tank 123. Reference numeral 135 designates the culture medium supply line and reference numeral 137 designates the culture medium recovery line.

Additionally, a cover 144 of the culture tank 123 is provided with pH adjuster liquid supply line 136 and a vent pipe 138, and there is provided below the culture tank 123 an exhaust port 140 for the culture medium.

Filling and exhausting of the cell matrix into and from the packed bed 125 are performed via respective ports extending through the side wall of the culture tank 123 and the packed bed 125. Reference numeral 142 designates the filling port and reference numeral 141 designates the exhausting port. It is preferred to position the filling port 142 above the exhausting port 141 since such arrangement facilitates filling and exhausting of the cell matrix.

Figure 11:
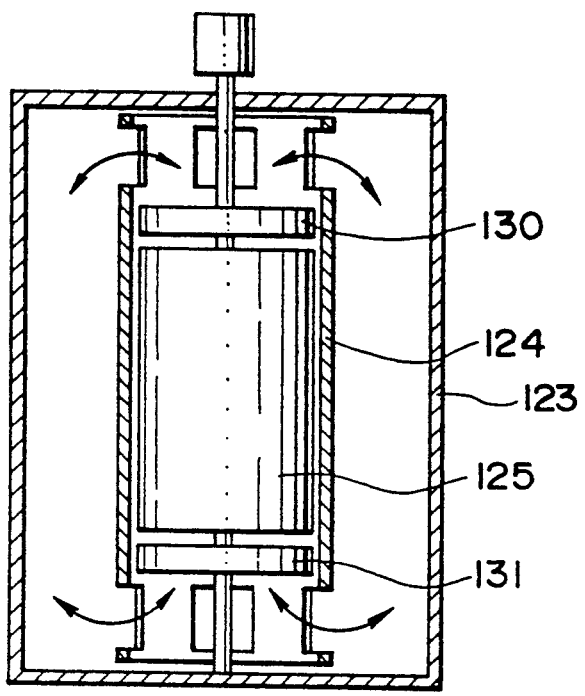
FIG. 11 is a sectional view illustrating how the system of FIG. 10 operates.
Figure 12:
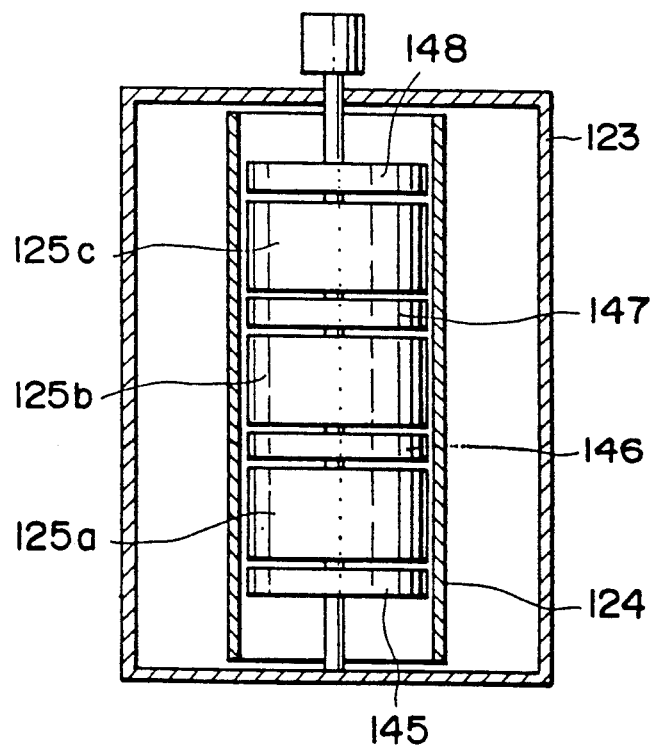
FIG. 12 is a view similar to FIG. 9 but illustrating a specific embodiment of the packed bed in the system of FIG. 10 arranged in a multistage fashion and provided between respective pairs of adjacent stages with rotary blades.

In this manner, the quantity of culture medium within the culture tank 123 is, after its nutrient, pH and DO have been adjusted, supplied to the packed bed 125 in order to proliferate the cells clinging to the cell matrix or to produce a target substance while the rotating direction of the blades 130, 131 is periodically switched and thereby the circulating direction of the culture medium is switched, as indicated by bidirectional arrows in FIG. 11. As in the embodiment shown by FIG. 12, the packed bed is arranged in a multistage fashion so that respective stages 125a, 125b, 125c are interposed between respective pairs of adjacent blades 145, 146, 147, 148 to improve a cultivating efficiency.

Each of the rotary blades employed by the third and fourth embodiments of the invention is preferably a turbine blade which is not only r.p.m. adjustable but also blade-angle adjustable in order to control a flow velocity of the culture medium. Usually, movement distance per unit time of the rotary blade is maximum at its outer end and minimum at its region closely adjacent the axis, so the flow velocity of the culture medium correspondingly varies. Accordingly, the blade-angle may be stepwise or continuously varied radially along its length to make the flow velocity of the culture medium within the culture tank substantially uniform in a plane of the rotary blade.

Furthermore, the rotary blade may be partially closed and supply of the culture medium may be performed only through the portion of the blade left open to pulsate the supply of the culture medium and thereby to avoid the channeling.

Finally, it should be understood that the cell cultivation of the invention utilizes the irregular-shaped ceramic particles as the cell matrix to hold the cells reliably and to keep the passage for the culture medium free, in view of a fact that the irregular-shaped particles can be effectively interlocked together to realize a stabilized condition though such carrier is not "fixed", strictly to say.

While the invention has been particularly shown and described with reference to preferred embodiments thereof, it will be understood by those skilled in the art that the foregoing and other changes in form and details can be made therein without departing from the spirit and scope of the invention.

What claimed is:

1. A process for cultivating adhesive cells in a packed bed of solid cell matrix comprising the steps of:
   (1) contacting adhesive cells with the solid cell matrix and adhering the cells to the matrix to provide an adhered cell solid matrix and packing the adhered cell solid matrix in a cell culture tank to form a packed bed thereof;
   (2) circulating culture medium through the packed bed in a direction wherein passages in the packed bed are formed and then stopping said circulation of the culture medium;
   (3) subsequently circulating the culture medium through the packed bed in a reverse direction wherein said passages are disrupted and new passages are formed and then stopping said circulation of the culture medium; and
   (4) sequentially repeating steps (2) and (3) to reduce channeling of the culture medium in the packed bed.

2. The process of claim 1 wherein the direction in which the culture medium is circulated through the packed bed in the cell culture tank is controlled by supplying the culture medium at an upper portion of the cell culture tank for a predetermined time and from a bottom portion of the cell culture tank for a predetermined time.

3. The process of claim 1, wherein during the step of circulating culture medium the oxygen content in the culture medium is determined.

4. The process of claim 2, further comprising a step of separating any bubble existing in the culture medium and any cell matrix passing from the cell culture tank by means of a separator provided near the bottom portion of the cell culture tank.

5. The process of claim 4, further comprising a step of separating any bubble existing in the culture medium by means of a separator provided near the upper portion of the cell culture tank so as to prevent such bubble from entering the cell culture tank.

6. The process of claim 1, wherein the solid cell matrix is ceramic particles and wherein the adhesive cells are gene-transduced rodential cells.

* * * * *